United States Patent [19]
Rotsaert

[11] Patent Number: 5,151,044
[45] Date of Patent: Sep. 29, 1992

[54] BLANKS FOR THE MANUFACTURE OF ARTIFICIAL TEETH AND CROWNS

[76] Inventor: Henri L. Rotsaert, 42 Brentwood Drive, Dundas, Ontario, Canada, L8T 3V8

[21] Appl. No.: 704,582

[22] Filed: May 22, 1991

Related U.S. Application Data

[60] Continuation of Ser. No. 511,500, Apr. 20, 1990, abandoned, which is a division of Ser. No. 350,964, May 12, 1989, Pat. No. 4,970,032.

[51] Int. Cl.⁵ .............................................. A61C 2/00
[52] U.S. Cl. ................................ 433/229; 433/202.1; 433/203.1
[58] Field of Search .................. 433/202.1, 203.1, 223, 433/228, 229

[56] References Cited

U.S. PATENT DOCUMENTS

| | | | |
|---|---|---|---|
| 1,511,459 | 10/1924 | Gibson | 433/202.1 |
| 2,585,858 | 2/1952 | Schwartz | 433/202.1 |
| 4,411,626 | 10/1983 | Becker et al. | 433/223 |
| 4,615,678 | 10/1986 | Moermann et al. | 433/173 |

*Primary Examiner*—John J. Wilson
*Attorney, Agent, or Firm*—Rogers & Scott

[57] ABSTRACT

A blank for the manufacture of artificial teeth, either replacement whole teeth or crowns, permits a tooth to be produced by machining from the blank which comprises a layered block of synthetic plastics materials, the layers being of predetermined varying color (hue), chroma, value and translucency to simulate the pulp, dentine and enamel layers in a real tooth, thereby providing an artificial tooth with the distribution and depth of color of a real tooth. The blank has a core portion including a reference point for machining purposes and the layers are applied over the core portion, their thicknesses and thickness distributions being predetermined so as to be able to obtain different tooth colors by selective removal from the layers. Thus, the tooth color is varied by milling the tooth from a different section of the layered block to vary the thicknesses of the layers, at least at the labial, mesial, distal and occlusal surfaces, and so as to obtain a custom tooth matched very closely to a patient's real tooth color and pattern. The teeth can be manufactured from materials with a hardness closely matching that of a real tooth to provide similar wear properties.

23 Claims, 8 Drawing Sheets

BLANKS FOR THE MANUFACTURE OF ARTIFICIAL TEETH AND CROWNS

CROSS-REFERENCE TO RELATED APPLICATIONS

This application is a continuation of my application Ser. No 07/511,500, filed Apr. 20, 1990, now abandoned, which is a division of application Ser. No. 07/350,964, filed May 2, 1989, now U.S Pat. No. 4,970,032, issued Nov. 13, 1990.

FIELD OF THE INVENTION

This invention relates to blanks for the manufacture of artificial teeth and crowns with colorings simulating as closely as possible those of real teeth.

BACKGROUND OF THE INVENTION

There are two main types of artificial teeth, namely crowns and denture teeth. Crowns are designed to fit a root stump which is left in the gum after the whole top part of the tooth has been removed, while denture teeth are intended to replace teeth which are no longer present. Denture teeth are usually attached to a bridge which extends between two teeth or to a plate which is worn against the upper or lower palate.

Crown teeth or crowns must be custom made because they must correspond at least approximately in shape to the teeth that they replace, and must fit whatever shape of stump is left for the attachment. Historically, crowns have been cast from a suitable metal which is left in its original color, so that the contrast with the natural teeth make them quite obvious. A more cosmetically acceptable crown is molded from ceramic material and then surface painted to match the surrounding teeth as closely as possible. Such crowns and the process by which they are made have a number of disadvantages. For example the process is very labour intensive and the painted-on color wears off in time. In addition, the ceramic materials from which these crowns are made are harder than natural teeth and this often results in accelerated wear of the opposing teeth. Finally, even with careful workmanship it is difficult to make the appearance of a painted tooth match that of the adjacent real teeth. Teeth are made up of three major layers, namely an interior pulp, a surrounding dentine, and an outer coating of enamel; the enamel and dentine are translucent so that all three layers contribute to the color which is visible from outside the tooth. The resulting depth and distribution of color in a natural tooth is very difficult to duplicate.

A new crown making technology which has recently become available provides a tooth body made from synthetic material, usually plastics, material which is shaped in a computer- controlled milling machine and then surface painted. The process is highly automated and provides great savings in labour, while another benefit is that the hardness of these teeth can be matched more closely to that of natural teeth. The problems of surface wear of the painted-on color and the less natural look of a painted-on surface are still present.

Denture teeth generally are not custom made, but instead are provided in a wide assortment of standard shapes, sizes and colors, from which the denture maker may choose. At one time most denture teeth were molded from homogeneous blocks of ceramic and surface painted in a manner similar to that described above for crown tooth manufacture. Current technology provides denture teeth which are molded with a number of internal successive colored layers, each of the layers contributing to the color which is visible on the outside of the tooth. This molding process provides a tooth with a depth and distribution of color more closely resembling that of a natural tooth, but requires at least three separate molds for each tooth and would be prohibitivly expensive in a custom process for producing individual crowns.

DEFINITION OF THE INVENTION

It is an object of the invention to provide new methods for custom manufacturing crowns and artificial teeth with color as close as possible to a natural tooth.

It is another object to provide an artificial tooth comprising a number of successive internal colored layers to simulate as closely as possible the coloring of a natural tooth.

According to the present invention there is provided a blank for the manufacture of an artificial tooth of a desired color comprising:

a core portion having lingual, labial, mesial, distal gingival and occlusal sides, the core portion approximating in shape at least at its labial, mesial and distal sides to the shape of a corresponding core portion of a tooth to be manufactured therefrom by removal of material from the blank;

reference means on the blank establishing a reference point from which the removal of material from the blank can be determined;

a first layer of another material overlaying at least the occlusial, labial, mesial and distal surfaces of the core portion;

a second layer of a further material overlaying at least the occlusial, labial, mesial and distal surfaces of the first layer;

the thicknesses of the said first and second layers and the distributions of their respective thicknesses over at least the said labial, mesial and distal sides cooperating together, and the materials of the core portion and of the first and second layers cooperating together, to provide at least at the labial, mesial and distal surfaces the required color for the tooth upon selective removal of material of the first and second layers from the blank to leave a tooth-shaped artificial tooth.

Preferably, the blank includes a third layer of a respective material overlying at least the labial, mesial and distal portions of the second layer, the thickness of the third layer, the distribution of its thickness, and the material thereof cooperating together with the thicknesses, thickness distributions and materials of the core portion and the first and second layers to provide the required color for the tooth.

Also in accordance with the invention there is provided a blank for the manufacture of an artificial tooth of a desired color comprising:

a core portion having lingual, labial, mesial, distal gingival and occlusal sides, the core portion approximating in shape at least at its labial, mesial and distal sides to the shape of a corresponding core portion of a tooth to be manufactured therefrom by removal of material from the blank;

reference means on the blank establishing a reference point from which the removal of material from the blank can be determined;

and a layer of another material overlaying at least the occlusial, labial, mesial and distal surfaces of the core portion;

the thicknesses of the core portion and of the said layer of another material and the distribution of their respective thicknesses over at least the said labial, mesial and distal sides cooperating together, and the materials of the core portion and the layer cooperating together, to provide at least at the labial, mesial and distal surfaces the required color for the tooth upon selective removal of material of the first layer from the blank to leave a tooth-shaped artificial tooth.

DESCRIPTION OF THE DRAWINGS

Particular preferred embodiments of the invention will now be described, by way of example, with reference to the accompanying diagrammatic drawings; wherein.

DESCRIPTION OF THE PREFERRED EMBODIMENT

The method of the invention can make use of a commercially available CADICAM milling system will permit milling of the teeth from a homogeneous block of plastics material which has the desired milling and wear characteristics. The patient's teeth are examined to determine the size and shape of the tooth or crown required, the surrounding and opposing teeth being also measured to ensure a correct replacement. The coloring of the surrounding teeth must also be determined so as to be able to make the new tooth match the existing tooth color as closely as possible. The measured parameters obtained from this examination are input into a computer control system which will guide the milling machine to develop the required tooth shape and color, as will be described below.

Figure 1:
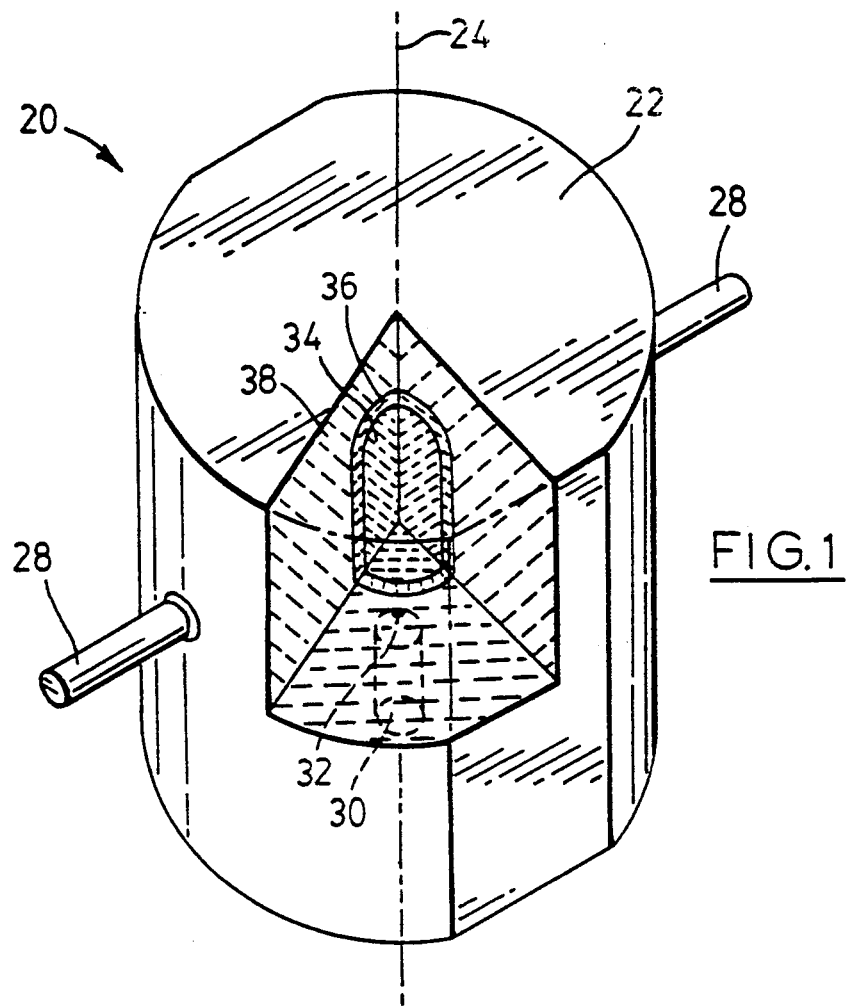
FIG. 1 is a perspective view of the exterior of a layered blank from which an artificial tooth can be produced by milling, part of the blank being cut away to reveal the internal layering.
Figure 2:
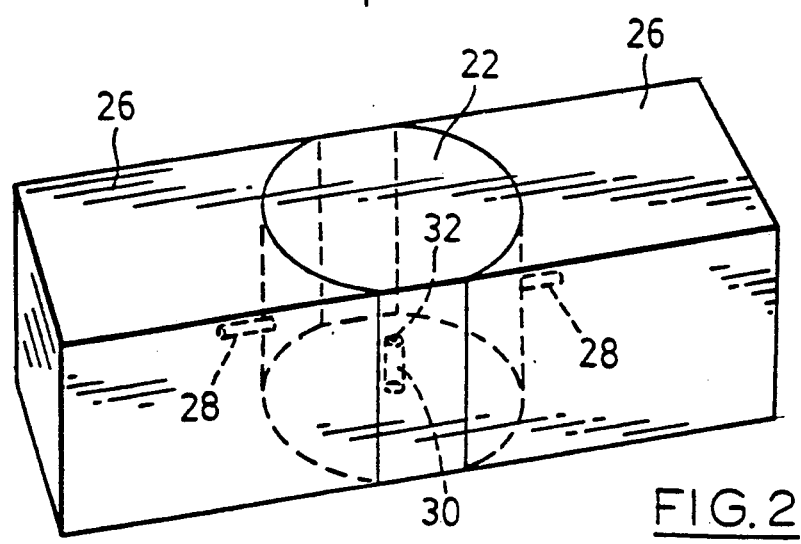
FIG. 2 is a perspective view of a tooth blank, comprising a layered block as in FIG. 1, which is used in the production of an artificial tooth.

The method employs a blank 20 as shown in FIG. 1 comprising a central portion 22 of standard shape, which in this embodiment is cylindrical with the cylindrical axis 24 extending occlusially-gingivally. This central portion is provided at its mesial and distal sides with two standard shaped wing portions 26 to form a complete blank as shown in FIG. 2, these wing portions constituting means by which the block is held in the milling machine for removal of material therefrom. The central portion is provided with mesially, distally extending protrusions 28 about which the wings are molded, as by injection molding. The central portion is also provided with an occlusially-gingivally extending bore 30 through which the axis 24 passes, the junction of this axis and the bottom surface of the bore constituting a reference point 32 to which all measurements of the milling machine can be referred to ensure the accuracy of the milling operation.

The central portion 22 is shown in FIG. 1 as having a segment cut away to show its interior, and it will be seen that there is a central core portion 34 which approximates in shape, at least at its labial, mesial and distal sides, to the shape of a corresponding core portion of the particular tooth to be manufactured from the blank by removal of material using the computer controlled milling machine. In this particular embodiment the tooth is one of the lower incisors. This central portion is overlaid, at least at its occlusial, labial, mesial and distal surfaces by a relatively thin first layer 36 of another material of different color to the core material. The layer 36 is in turn overlaid by a second layer 38 of another material of a different color from the other two materials, this second layer being made sufficiently thick that it forms the desired cylindrical shape of the central portion 22. Such a blank is readily made by injection-moulding the core and the layers in successive operations.

Figure 3:
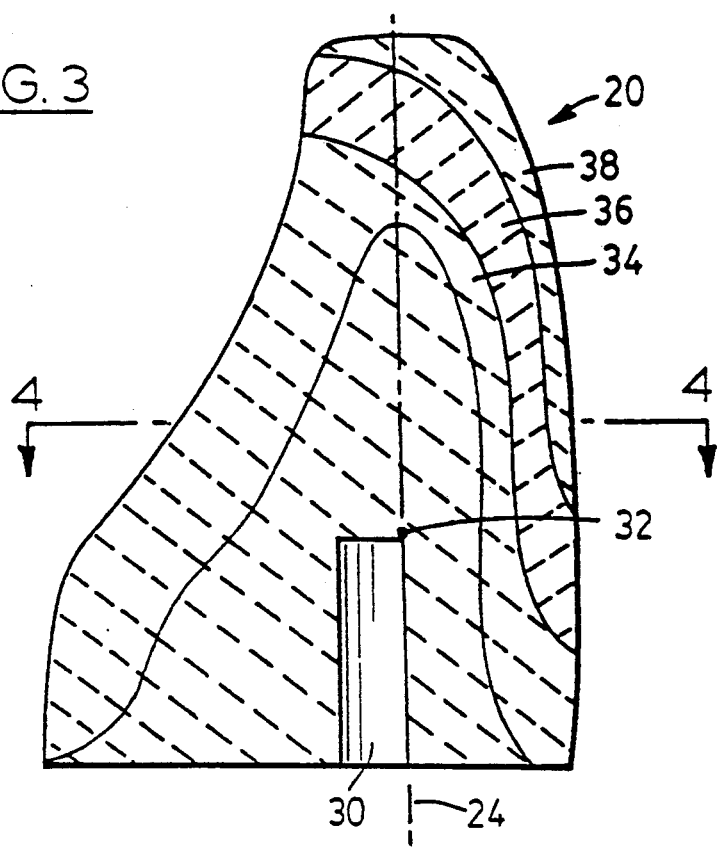
FIG. 3 is a cross-sectional view in an occlusial-gingival extending plane of an incisor tooth showing a preferred arrangement of the successive colored layers in the manufactured tooth.
Figure 4:
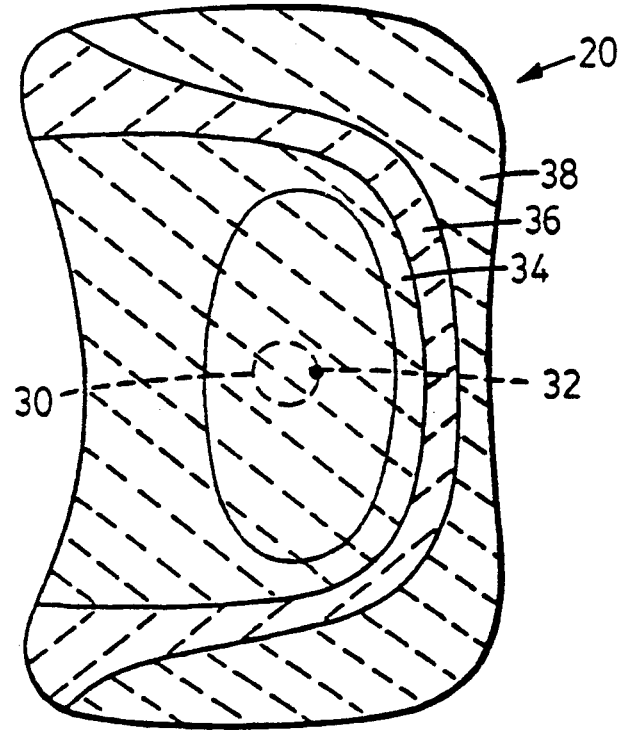
FIG. 4 is a cross-sectional view of the tooth of FIG. 3 in a mesial-distal plane, taken on the line 4-4 in FIG. 3.

The blank is mounted in the milling machine and the tooth shape is now milled therefrom so as to provide at the occlusical, labial, mesial and distal surfaces of the core portion 34 the thicknesses of the layers 36 and 38 such that with their color and translucency the resultent incisor tooth will have as closely as possible the desired color to match the adjoining teeth, without the need to paint color on the external surface, as in the prior art methods. The cross-section through such a tooth, taken in the occlusal-gingival extending plane is shown in FIG. 3, while the corresponding mesial-distal cross-section is shown in FIG. 4. It will be seen that the gingival and lingual surfaces of the tooth are constituted by the material of the shoulder or central core portion 34, so that there is no control of the color of these two surfaces, but this is immaterial since the gingival surface abuts the tooth stump to which the crown is fastened, and the lingual surface is only seen by someone inspecting the interior of the mouth, such as the prosthodontist.

The blank preferably is made by injection molding the different colored materials one on the other from suitable plastics materials such as acrylics, polyurethanes, dimelthylacrylates, and composites thereof. All three materials of the different layers can be of the same chemical composition, with the exception of the inclusion therein of different fillers to provide the different colors and translucency that are required to provide a suitable range of tooth colors from a single blank. It will usually be necessary to provide a number of different blanks for the full range of replacement teeth that must be provided, owing to differences in size, basic color and color distribution. Since the central core portion 34 approximates the basic shape of the tooth to be manufactured, it will be seen that different blanks will also be required for the other tooth shapes present in the human mouth, namely the canines, bicuspids and molars, both upper and lower.

Figure 5:
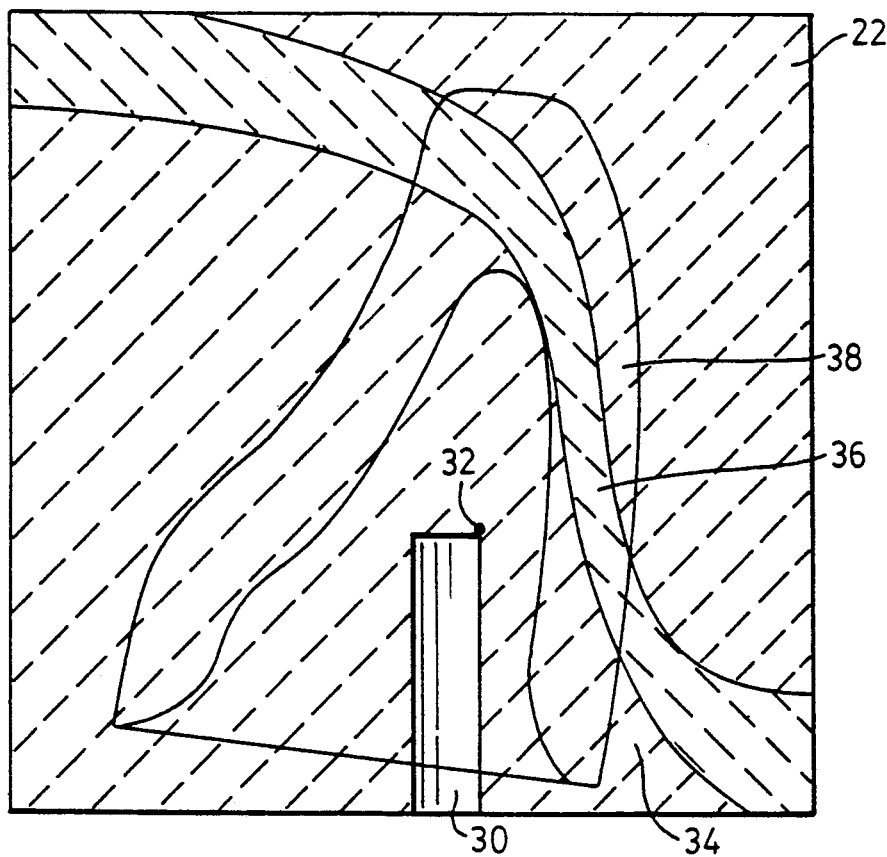
FIG. 5, 6 and 7 are cross-sections taken in the same plane as FIG. 3 showing the arrangement of layers in the layered block as seen in this plane, and with different outlines of an incisal tooth, as seen from the mesial or distal direction, superimposed on different portions of the layered block to provide different arrangements of layers and thereby provide different colorings for the tooth.
Figure 6:
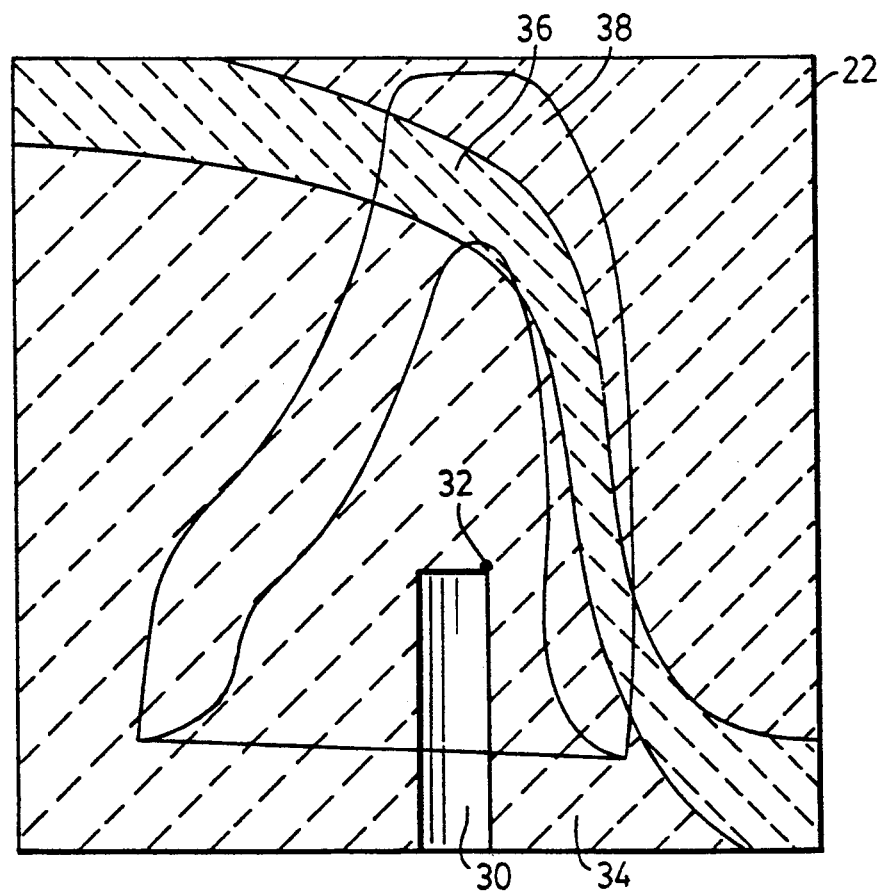
Figure 7:
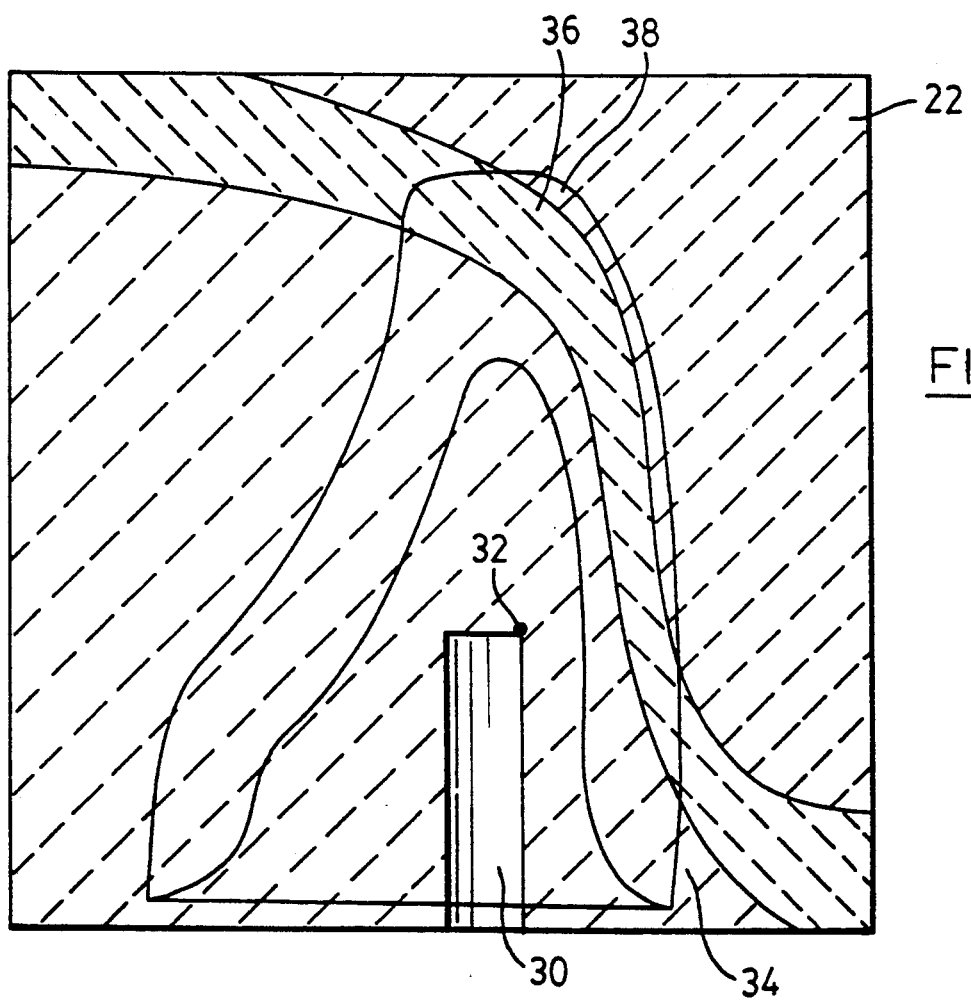

FIGS. 5, 6 and 7 illustrate the manner in which different tooth colors and color distributions can be achieved from the same basic shoulder or core portion 34 and layers 36 and 38. Thus, in the tooth of FIG. 5 the profile is tilted toward the labial and extends close to the gingival surface, so that the layer 38 is relatively thick at the incisal occlusal surface and the upper part of the labial surface, while the gingival portion of the labial surface is provided by the layers 36 and the core 34. The profile in FIGS. 6 and 7 is more upright and are respectively closer to the occlusal and gingival surfaces, thereby correspondingly varying the thicknesses and thickness distribution of the layers 36 and 38 and the resultant tooth color and color distribution. It will be seen therefore that in these particular embodiments the three material layers 34, 36 and 38 can be regarded as corresponding respectively approximately to the pulp, dentine and enamel (incisal material) of the human tooth and their thicknesses and transparency or translucency, particularly of the two layers 36 and 38, can be adjusted to give the equivalent color (hue) and color density or saturation (chroma) of the tooth which is replaced by the artificial tooth. As the outer layer is thinner, then the color and translucency of the underlying layers contributes more to the color of the tooth as seen by the observer, as with the pulp, dentine and enamel of natural teeth. The hardness of the material is of course chosen to approximate as closely as possible that of the human tooth it replaces, so that its wear characteristic will be similar to that of the adjacent teeth, and its characteristic change of color with age and wear will also be similar.

Figure 8:
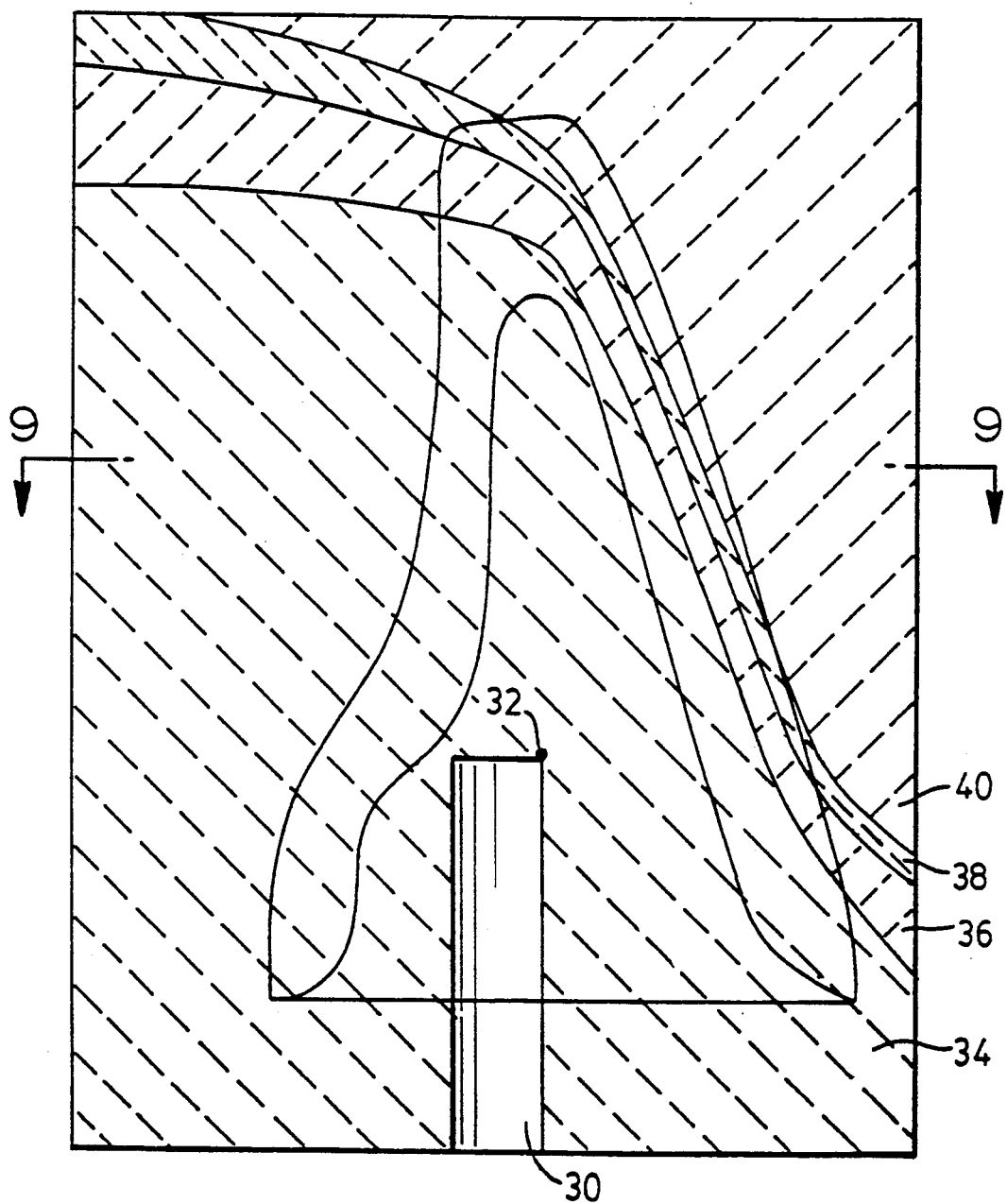
FIGS. 8 and 9 are views similar to FIGS. 3 and 4 respectively of a different embodiment employing an additional intermediate layer.
Figure 9:
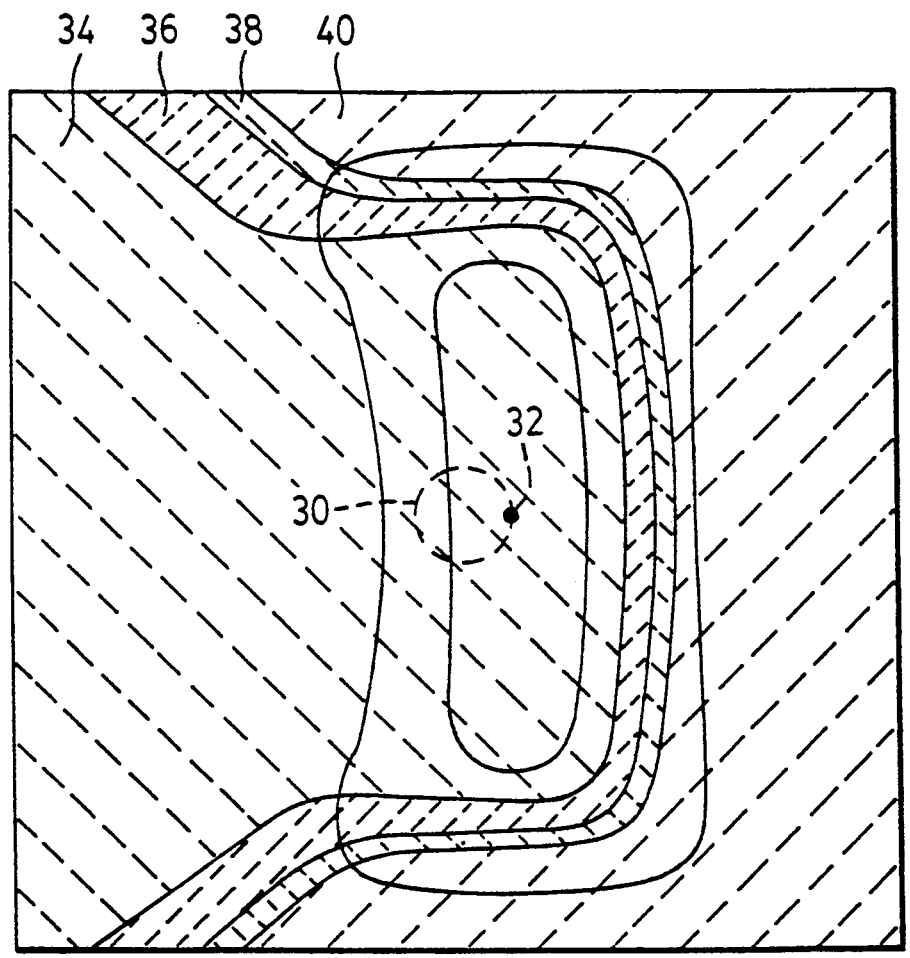

FIGS. 8 through 11 show a further development of the invention in which the core 34 is provided, at least overlying its occlusal, labial, mesial and distal surfaces, with three superimposed layers 36, 38 and 40, the last layer 40 being the layer that is extended to form the block of standard external size, which with these embodiments can be rectangular in plan and elevation. FIG. 8 shows a mesial-distal view of the tooth in an occlusal-gingival plane and it will be seen that the lingual surface is almost entirely within the core 34, except close to the occlusal end. The occlusal incisal surface is provided by the two layers 38 and 40, while the labial surface starts occlusially with the outer layer 40 and crosses the layers 38 and 36 to terminate at its gingival end in the core material 34. FIG. 9 is an occlusal view of FIG. 8 taken on the line 9—9 in FIG. 8.

Figure 10:
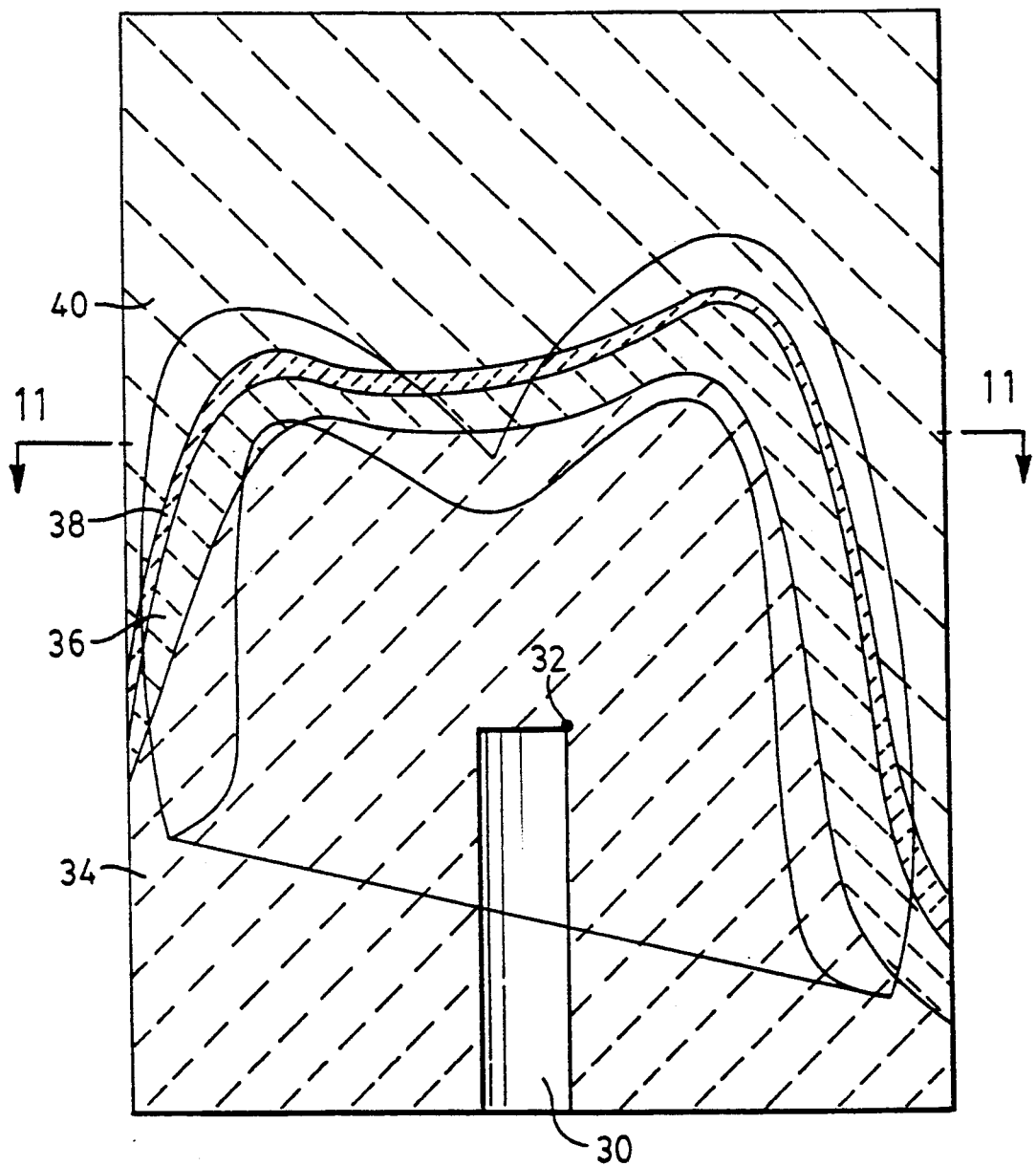
FIGS. 10 and 11 are views similar to FIGS. 8 and 9 respectively and showing the block in conjunction with the outline of a bicuspid tooth superimposed thereon.
Figure 11:
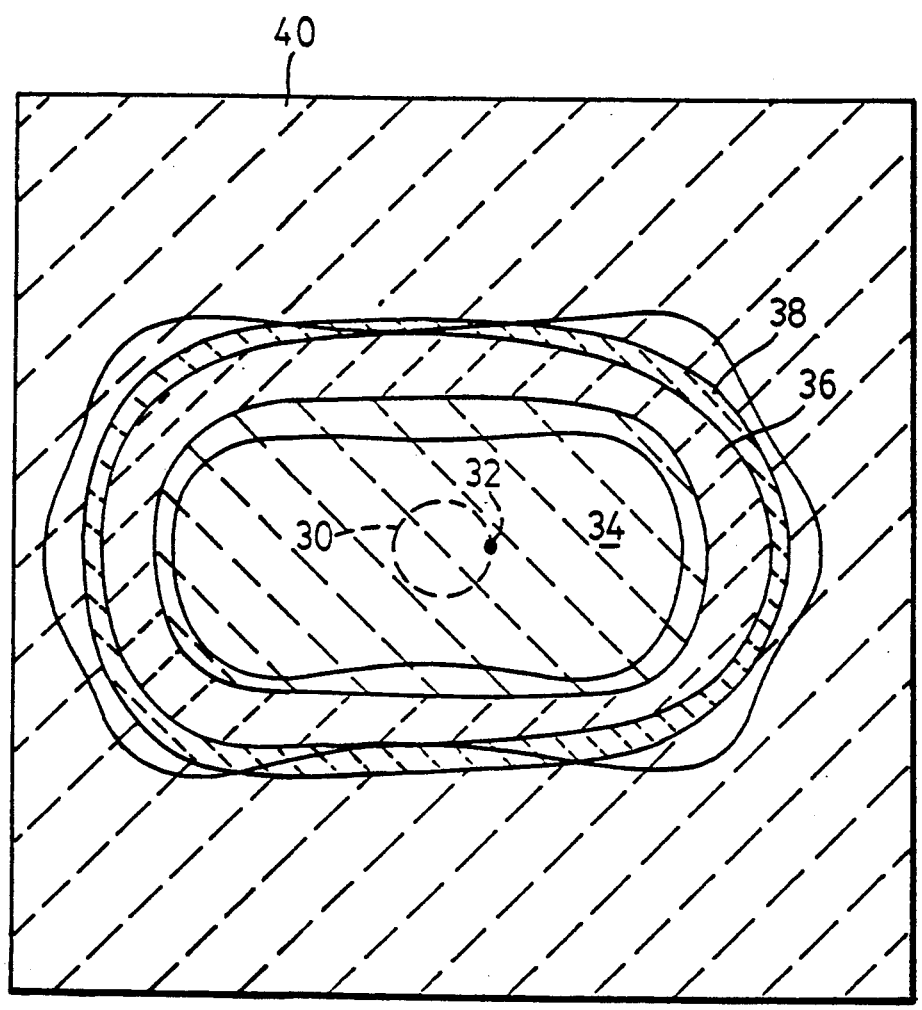

FIG. 10 is a similar cross section to FIG. 8 of a block intended for the production of a bicuspid tooth crown and showing the profile thereof, while FIG. 11 is an occlusal view taken on the line 11-11 in FIG. 10.

Although the invention has so far been described in its application to the production of replacement crowns, it is equally applicable to the production of replacement denture teeth, when each tooth will be provided with a suitable root portion to facilitate its mounting in the supporting plate or bridge.

The provision of four layers provides even greater flexibility in obtaining the desired tooth color and color distribution. The color is sometimes in the industry referred to as the hue, while the value is the gray scale value for a particular color. The color density or saturation is referred to as the chroma. There are a number of systems already employed in the industry to characterize tooth color for replacement teeth and crowns, such as the Lumin Vac Shade Guide of Vita G.m.b.H, to which reference can be made.

The core material 34 can have its own distinctive color since it will frequently appear at least at the gingival end of the labial surface, or it can be given the desired dentine or base color. The first layer 36 can instead or in addition be given the base or dentine color, while the second layer 38 can be an intermediate dentine color to give the desired wider variation. The third layer 40 simulates the incisal material and is colored appropriately, or in some embodiments can be completely clear, particularly with blanks for the production of anterior teeth.

In a particular preferred embodiment intended for the manufacture of an incisal tooth, as illustrated by FIG. 8 the block 22 may measure about 9 cm in the mesial-distal direction, and about 1.2 cm in both the occlusal-gingival and labial-lingual directions. The replacement tooth for an upper central incisor typically measures about 9.5 mm occlusially-gingivally, about 1.5 mm labially-lingually at the occlusal surface, about 6.5 mm labially-lingually at the gingival surface, and about 8 mm mesially-distally. In such an embodiment the first layer 36 may have a thickness of about 0.3 mm at the labial surface increasing progressively at the occlusal surface to about 0.75 mm, and also increasing progressively at the gingival end to about the same. The second layer 36 may have a thickness of about 0.2 mm at the labial surface increasing progressively to about 0.5 mm at the occlusal and gingival ends.

I claim:

1. A blank for the manufacture therefrom of a single artificial tooth of a desired color by the removal of material from the blank, the blank comprising:

a core portion having lingual, labial, mesial, distal gingival and occlusal sides, the core portion approximating in shape at least at its libial, mesial and distal sides to the shape to a corresponding core portion of a single tooth to be manufactured therefrom;

reference means on the blank establishing a reference point from which the removal of material from the blank can be determined;

a first layer of another material overlaying at least the occlusal, labial, mesial and distal surfaces of the said core portion, a second layer of a further material overlaying at least the occlusal, labial, mesial and distal surfaces of the first layer;

the thickness of the said first and second layers and the distributions of the their respective thicknesses over at least the said labial, mesial and distal sides cooperating together, and the materials of the said core portion and of the first and second layers cooperating together, to provide at least at the labial, mesial and distal surfaces the required color for the tooth upon selective removal of material of the first and second layers from the blank to leave a single tooth-shaped artificial tooth.

2. A blank as claimed in claim 1, wherein the material of the first layer simulates the dentine of a tooth and the material of the second layer simulates the incisal material of a tooth.

3. A blank as claimed in claim 1, wherein the second layer has a shape to form a block of standard external size and shape irrespective of the sizes and shapes of the core portion and the first layer.

4. A blank as claimed in claim 3, wherein the blank includes on its mesial and distal sides two shaped wing portions constituting means by which the block is held in a machine for removal of material from the blank.

5. A blank as claimed in claim 1, wherein the reference means for the blank is a bore within the core portion opening to its gingival side, the reference point being at the bottom of the bore.

6. A blank as claimed in claim 1, wherein the materials of the core portion and of the first and second layers are of the same chemical composition and differ from one another in color, and wherein the different colors correspond respectively to those required to simulate the pulp, dentine and enamel of natural teeth.

7. A blank as claimed in claim 1, wherein the core portion and the first and second layers are formed by injection molding from plastics material or materials.

8. A blank as claimed in claim 1, and including a third layer of a respective material overlying at least the labial, mesial and distal portions of the second layer, the thickness of the third layer, the distribution of its thickness, and the material thereof cooperating together with the thicknesses, thickness distributions and materials of the core portion and the first and second layers to provide the required color for the tooth.

9. A blank as claimed in claim 8, wherein the material of the first layer simulates the dentine of a tooth and the material of the third layer simulates the incisal material of a tooth.

10. A blank as claimed in claim 8, wherein the third layer has a shape to form a block of standard external size and shape irrespective of the sizes and shapes of the core portion and the first and second layers.

11. A blank as claimed in claim 10, wherein the blank includes on its mesial and distal sides two shaped wing portions constituting means by which the block is held in a machine for removal of material from the blank.

12. A blank as claimed in claim 8, wherein the reference means for the blank is a bore within the core portion opening to its gingival side, the reference point being at the bottom of the bore.

13. A blank as claimed in claim 8, wherein the materials of all of the layers are of the same chemical composition and differ from one another only in their color.

14. A blank as claimed in claim 8, wherein the materials of the core portion and all of the layers are of the same chemical composition and differ from one another only in their color.

15. A blank as claimed in claim 8, wherein the materials of the core portion and the first, second and third layers differ from one another in color, the color of the core portion corresponding to that of the pulp or the dentine of natural teeth, the color of the first layer corresponding to that of pulp or dentine of natural teeth, the color of the second layer also corresponding to that of dentine of natural teeth, and the color of the third layer corresponding to that of the enamel of natural teeth.

16. A blank as claimed in claim 8, wherein the core portion and the first, second and third layers are formed by injection molding from plastics material or materials.

17. A blank for the manufacture therefrom of a single artificial tooth of a desired color by the removal of material from the blank, the blank comprising:

a core portion having lingual, labial, mesial, distal gingival and occlusal sides, the core portion approximating in shape at least at its libial, mesial and distal sides to the shape of a corresponding core portion of a single tooth to be manufactured therefrom;

reference means on the blank establishing a reference point from which the removal of material from the blank can be determined;

and a layer of another material overlaying at least the occlusal, labial, mesial and distal surfaces of the said core portion;

the thickness of the said core portion and of the said layer of another material and the distribution of their respective thicknesses over at least the said labial, mesial and distal sides cooperating together, and the materials of the core portion and the layer cooperating together, to provide at least at the labial, mesial and distal surfaces the required color for the tooth upon selective removal of material of the first layer from the blank to leave a tooth-shaped artificial tooth.

18. A blank as claimed in claim 17, wherein the material or the core portion simulates the dentine or a tooth and the material of the layer simulates the incisal material of a tooth.

19. A blank as claimed in claim 17, wherein the material of another layer has a shape to form a block of standard external size and shape irrespective of the size and shape of the core portion.

20. A blank an claimed in claim 17, wherein the blank includes on its mesial and distal sides two shaped wing portions constituting means by which the block is held in a machine for removal of material from the blank.

21. A blank as claimed in claim 17, wherein the reference means for the blank is a bore within the core portion opening to its gingival side, the reference point being at the bottom of the bore.

22. A blank as claimed in claim 17, wherein the materials of the core portion and the layer are of the same chemical composition and differ from one another only in their color.

23. A blank as claimed in claim 17, wherein the core portion and the layer are formed by injection molding from plastics material or materials.

* * * * *